United States Patent
Estripeau

(10) Patent No.: US 12,200,590 B2
(45) Date of Patent: *Jan. 14, 2025

(54) APPARATUS FOR LOCATING AN AEROSOL GENERATION DEVICE

(71) Applicant: JT International S.A., Geneva (CH)

(72) Inventor: Frederic Claude Hervé Estripeau, Divonne les Bains (FR)

(73) Assignee: JT International S.A. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/242,345

(22) Filed: Sep. 5, 2023

(65) Prior Publication Data

US 2024/0147205 A1    May 2, 2024

Related U.S. Application Data

(63) Continuation of application No. 17/839,634, filed on Jun. 14, 2022, now Pat. No. 11,785,437, which is a
(Continued)

(30) Foreign Application Priority Data

Dec. 18, 2017   (EP) ..................................... 17208194

(51) Int. Cl.
*H04W 4/80* (2018.01)
*A24F 40/53* (2020.01)
(Continued)

(52) U.S. Cl.
CPC .............. *H04W 4/80* (2018.02); *A24F 40/53* (2020.01); *A24F 40/65* (2020.01); *A61M 15/06* (2013.01);
(Continued)

(58) Field of Classification Search
CPC ......... H04W 4/80; H04W 4/029; A24F 40/53; A24F 40/65; A61M 15/06; G01S 5/0027
See application file for complete search history.

(56) References Cited

U.S. PATENT DOCUMENTS 7,437,167 B2   10/2008  Kartchner
8,918,272 B2   12/2014  DeMerchant et al.
(Continued)

FOREIGN PATENT DOCUMENTS

CN    105472533 A    4/2016
CN    107018490 A    8/2017
(Continued)

OTHER PUBLICATIONS

Search Report dated Nov. 13, 2023 from the Office Action for Chinese Application No. 202111458927.6, pp. 1-2.
(Continued)

*Primary Examiner* — John A Tweel, Jr.
(74) *Attorney, Agent, or Firm* — Lerner David LLP

(57) ABSTRACT

A system is disclosed comprising a smartphone 2 and an aerosol generation device, such as an electronic cigarette. The smartphone 2 is configured to establish a communicative interaction with the electronic cigarette 4, preferably using a wireless protocol like Bluetooth® so that the devices can exchange data. The smartphone 2 comprises a positioning module, such as a GPS receiver 26, and is adapted to store a position in a data storage unit 28 each time a communicative interaction is established. In this way, the user can retrieve the last stored position from the data storage unit 28 and display it on a map on the smartphone display screen 22 so that they can be assisted in locating the electronic cigarette 4.

21 Claims, 7 Drawing Sheets

Related U.S. Application Data continuation of application No. 16/993,711, filed on Aug. 14, 2020, now Pat. No. 11,368,831, which is a continuation of application No. 16/707,793, filed on Dec. 9, 2019, now Pat. No. 10,782,383, which is a continuation of application No. PCT/EP2018/085644, filed on Dec. 18, 2018.

(51) Int. Cl.
| | |
|---|---|
| *A24F 40/65* | (2020.01) |
| *A61M 15/06* | (2006.01) |
| *G01S 5/00* | (2006.01) |
| *H04W 4/029* | (2018.01) |
| *A24F 40/10* | (2020.01) |

(52) U.S. Cl.
CPC ........... *G01S 5/0027* (2013.01); *H04W 4/029* (2018.02); *A24F 40/10* (2020.01)

(56) References Cited

U.S. PATENT DOCUMENTS

| | | | |
|---|---|---|---|
| 9,357,348 | B2 | 5/2016 | Evans et al. |
| 9,473,488 | B2 | 10/2016 | Wu |
| 9,936,734 | B2 | 4/2018 | Hawes et al. |
| 10,321,711 | B2 | 6/2019 | Henry, Jr. et al. |
| 10,440,517 | B2 | 10/2019 | Baker et al. |
| 10,782,383 | B2 | 9/2020 | Estripeau |
| 10,888,125 | B2 | 1/2021 | Anderson et al. |
| 11,368,831 | B2 | 6/2022 | Estripeau |
| 11,686,858 | B2 * | 6/2023 | Estripeau ........... G06Q 30/0639 705/26.9 |
| 11,785,437 | B2 * | 10/2023 | Estripeau ................ H04W 4/80 340/539.13 |
| 2007/0045288 | A1 | 3/2007 | Nelson |
| 2013/0319439 | A1 | 12/2013 | Gorelick et al. |
| 2014/0174459 | A1 | 6/2014 | Burstyn |
| 2015/0100441 | A1 | 4/2015 | Alarcon et al. |
| 2015/0114407 | A1 | 4/2015 | Duncan et al. |
| 2015/0126234 | A1 | 5/2015 | Rodriguez |
| 2015/0181945 | A1 | 7/2015 | Tremblay |
| 2016/0189523 | A1 | 6/2016 | Neumeyer et al. |
| 2016/0337141 | A1 | 11/2016 | Cameron |
| 2016/0337444 | A1 | 11/2016 | Cameron |
| 2016/0351044 | A1 | 12/2016 | Liu |
| 2016/0363917 | A1 | 12/2016 | Blackley |
| 2017/0071262 | A1 | 3/2017 | Liu |
| 2017/0093960 | A1 | 3/2017 | Cameron |
| 2017/0134898 | A1 | 5/2017 | Vega et al. |
| 2017/0156397 | A1 | 6/2017 | Sur et al. |
| 2017/0164156 | A1 | 6/2017 | Evans et al. |
| 2018/0286208 | A1 | 10/2018 | Baker et al. |
| 2019/0174266 | A1 | 6/2019 | Baker et al. |
| 2020/0000143 | A1 | 1/2020 | Anderson et al. |
| 2020/0093180 | A1 | 3/2020 | Qiu |
| 2020/0229492 | A1 | 7/2020 | Wilson et al. |
| 2022/0028245 | A1 | 1/2022 | Smith et al. |

FOREIGN PATENT DOCUMENTS

| | | |
|---|---|---|
| KR | 101570106 B1 | 11/2015 |
| KR | 101609715 B1 | 4/2016 |
| TW | I607418 B | 12/2017 |
| WO | 2014/106096 A1 | 7/2014 |
| WO | 2014/205456 A2 | 12/2014 |
| WO | 2015/175701 A1 | 11/2015 |
| WO | 2016/025634 A1 | 2/2016 |
| WO | 2016/168400 A1 | 10/2016 |
| WO | 2017055799 A1 | 4/2017 |
| WO | 2017/182976 A1 | 10/2017 |
| WO | 2017205692 A1 | 11/2017 |

OTHER PUBLICATIONS

Partial International Search Report for PCT/EP2018/085644 dated Mar. 6, 2019.
The Dallas Morning News, "Tech Review: The Tile" Jun. 11, 2015, [cited Jul. 13, 2023] Available from: [https://www.youtube.com/watch?v=Btlmak_-_es].
Immersive Tech TV, "Best Key Finder?—Tile Mate Tracker Review" Apr. 24, 2017, [cited Jul. 13, 2023] Available from: [https://www.youtube.com/watch?v=FRYRfi6sf14].
Amazon, "Amazon.deKundenrezensionen Tile (Gen 2)—1 Packung—vomHersteller eingestellt" Feb. 15, 2016, [cited Dec. 16, 2022] Available from: [https://www.amazon.com/gp/aw/reviews/B011HT9AL27].
Bestbuy, "Customer Reviews: Title Item Tracker White TLE-01001-NA- BestBuy" May 13, 2016, [cited Dec. 16, 2022] Available from: [https://www.bestbuy.com/site/reviews/tile-item-tracker-white/4546500?page=14].
Albertson, Jeff, "Remember where you parked with Google Maps" Apr. 25, 2017, [cited Jul. 11, 2023]; Available from: [https://blog.google/products/maps/remember-where-you-parked-google-maps/].
The Britannica Dictionary, "When to use "in" and "on"", [cited May 16, 2023] Available from: [https://www.britannica.com/dictionary/eb/qa/When-to-use-prepositions-in-andon#:-:text=IN].
Pierson, William R., and Wanda W. Brachaczek. "Particulate matter associated with vehicles on the road. II", Aerosol Science and Technology 2, No. 1 (1983), pp. 1-40.
Bluetooth, "Bluethooth Core Specification", Covered Core Package Version 5.0. Dec. 6, 2016. 2822 pgs.
Communication of a notice of opposition for European Application No. 18822342.4 dated Jul. 21, 2023. 74 pgs.
Communication of a notice of opposition for European Application No. 18822342.4 dated Jul. 26, 2023. 102 pgs.
Communication of a notice of opposition for European Application No. 22201053.0, dated Jul. 31, 2024, pp. 1-91.
Communication of a notice of opposition for European Application No. 22201053.0, dated Aug. 2, 2024, pp. 1-139.

\* cited by examiner

APPARATUS FOR LOCATING AN AEROSOL GENERATION DEVICE

CROSS-REFERENCE TO RELATED APPLICATIONS

The present application is a continuation of U.S. patent application Ser. No. 17/839,634 filed Jun. 14, 2022, now U.S. Pat. No. 11,785,437, which is a continuation of U.S. patent application Ser. No. 16/993,711 filed Dec. 6, 2020, now U.S. Pat. No. 11,368,831, which is a continuation of U.S. patent application Ser. No. 16/707,793, filed Dec. 9, 2019, now U.S. Pat. No. 10,782,383, which is a continuation of International Application No. PCT/EP2018/085644, filed Dec. 18, 2018, which claims priority from European Patent Application No. 17208194.5, filed Dec. 18, 2017, the disclosures of which are hereby incorporated herein by reference.

BACKGROUND

The present invention relates to an apparatus and method for improving the ease with which a user can locate an aerosol generation device, such as an electronic cigarette.

Electronic cigarettes and other aerosol generation devices are becoming increasingly popular among consumers. Unlike conventional cigarettes, which are consumed, an electronic cigarette is intended to be re-filled and used many times. Electronic cigarettes have a high unit cost, in comparison to conventional cigarettes, and therefore more care is required by users to ensure that they do not become lost.

An object of the present invention is to assist a user in locating an aerosol generation device, such as an electronic cigarette.

According to an aspect of the invention there is provided a system comprising: a positioning module arranged on a user electronic device; a communication interface to provide a communicative interaction with an aerosol generation device; and a data storage module, wherein the data storage module is configured to store a position determined by the positioning module, and wherein the stored position is associated with the communicative interaction with the aerosol generation device, wherein the position may be stored based on a trigger, which may comprise one or more of the following: upon establishing or during a communicative interaction with the aerosol generation device; and following termination of a communicative interaction with the aerosol generation device.

In this way, the system can assist a user in locating the aerosol generation device. This can be done in a cost effective way since the need for a further positioning module on the aerosol generation device is obviated. When the aerosol generation device cannot be located easily the stored position can be retrieved from the data storage module. The stored position may be indicative of an assumed position of the aerosol generation device, based on the position of the electronic user device during or shortly after the communicative interaction.

In addition, the system can determine whether a trigger event has occurred, and only store the position once this condition has been satisfied. In one example the trigger may be the aerosol generation device transitioning into an inactive mode such as a standby mode. An inactive mode may be determined after a period of inactivity has elapsed or after the aerosol generation device has been placed in an inoperative configuration. One example of an inoperative configuration may be where the mouthpiece has been retracted into the device body, which can be considered as a last puff of the device before the device enters the inactive mode.

The data storage module may be provided in the electronic user device. In an alternative the data storage module may be provided remotely, for example in a server, which can be accessed by the electronic user device when required.

The stored position may be associated with a most recent communicative interaction with the aerosol generation device. The stored position may be the "last known position" of the aerosol generation device. In reality the stored position may be a rough approximation of the position of the aerosol generation device when it was last in communication with the connection interface, and this information may be useful for the user in locating the aerosol generation device.

In an alternative arrangement the stored position may be the most common position associated with communicative interactions with the aerosol generation device. It may also be possible to store an average position associated with communicative interactions with the aerosol generation device.

Preferably the electronic user device comprises a display configured to indicate the stored position. In this way the stored position can be retrieved from memory and indicated to the user on a display.

The display may be configured to indicate the stored position on a map. In one arrangement the display may be configured to indicate the current position of the user, as determined by the positioning module, as well as the stored position. In this way, the user can be assisted in finding the aerosol generation device, based on its last known position. The electronic user device preferably comprises a processor that generates the instructions for an indication to be displayed on the map, where the indication is indicative of the stored position.

The indication of the stored position on the map may be changed when communicative interaction is established with the aerosol generation device. In one arrangement the indication on the map may become selectable by a user on the display.

A notification may be provided by the electronic user device when a communicative interaction is established with the aerosol generation device. The notification may include one or more of the following: haptic feedback; audible feedback; and visual feedback, including on the display. In one arrangement an icon associated with the aerosol generation device (e.g. the indication on the map) may become selectable when communicative interaction is established. The icon may provide feedback to the user indicating that communicative interaction has been established, e.g. by one or more of a change in size, shape or colour. In this way a user may firstly coarsely locate the aerosol generation device by moving to the stored position before any connection has been established. Subsequently, when the position of the user is close enough to the aerosol generation device, the user may be notified of the establishment of a connection between the electronic user device and aerosol generation device, so that they can more precisely locate the aerosol generation device.

The data storage module may be configured to store a position determined by the positioning module based on data received from the aerosol generation device in the communicative interaction. Thus, the receipt of data, or at least a certain type or pattern of data, from the aerosol generation device may be processed as an instruction for the electronic user device to store a position in the data storage module. In one example, the determination of a vape through the aerosol generation device (including termination or initiation of a vape) may trigger the electronic user device to store a position. Vaping may be determined by a flow sensor, a vaping button or other means. This may be helpful in prompting data exchange between the aerosol generation device and the user device, and a position may be determined on each or a predetermined number of occasions. This can allow the stored position to be updated, and the latest stored position may represent an assumed position of the aerosol generation device.

Preferably the position associated with the aerosol generation device is stored along with identifying information for the aerosol generation device. For example, the position may be stored along with the model and/or serial number of the aerosol generation device. This can allow a user to distinguish devices, in case they own several.

Preferably the positioning module includes a Global Navigation Satellite System (GNSS) receiver. Alternatively, or in addition, the positioning module may include an inertial sensor, or a receiver for determining position using Wi-Fi or telecommunications signals.

The communication interface may be arranged to establish communicative interaction between the electronic user device and the aerosol generation device using a wireless protocol such as Bluetooth or Wi-Fi. A wired connection may also be established between the electronic user device and the aerosol generation device. As used herein "communicative interaction" may refer to: information transfer between devices; pairing; authentication; establishing of a data session or dialogue; or termination of a connection.

The system may further comprise an aerosol generation device. In one embodiment an indication may be provided by the aerosol generation device when communicative interaction is established with the connection interface or during the communicative interaction. The indication may be one or more of: visual, using a light or other indicator; audible; haptic; or other like indication.

In an embodiment the aforementioned icon displayed on the electronic user device (or other element) is or becomes user selectable when a connection is established. Selection of said icon may trigger the indication by the aerosol generation device. In this way a user may firstly coarsely locate the aerosol generation device by moving to the stored position. Subsequently, the user may trigger the indication by the aerosol generation device to more precisely locate said device. An indication, which may be audible and/or haptic, may be provided by the aerosol generation device, which has a property that is dependent on the separation distance between the aerosol generation device and the electronic user device. The separation distance may be determined based on the strength of the wireless signal received at the connection interface or the aerosol generation device, as appropriate, e.g. by received signal strength indication (RSSI indicator). The indication may assist a user in locating the aerosol generation device. In one example, an audible indication may have a frequency that depends on the separation distance, and the frequency may be higher when the separation distance is small. The frequency may refer to the pitch of the indication or the rate of repetition of the indication. The audible indication may be provided by a vibration of the aerosol generation device.

Typically the indication is provided on a display of the electronic user device. The indication may include a determined numerical distance to the aerosol generating device and/or an icon that changes colour (e.g. from blue to red) based on proximity. An advantage is that the indication of the electronic user device may be used if the indication of the aerosol generating device is obscured.

Preferably the indication provided by the aerosol generation device can be inhibited by a user. The indication can be inhibited either using the aerosol generation device or the electronic user device. On the aerosol generation device a button may be activated to indicate that it has been located, and to inhibit the indication. A similar button may be provided on the display of the electronic user device.

Preferably the indication provided by the aerosol generation device is inhibited during use of the aerosol generation device. Thus, the indication can be inhibited during vaping. This may be detected by depression of a vaping button, or activation of an air pressure sensor.

In one arrangement the electronic user device may be configured to provide a beaconing signal using the connection interface, and the aerosol generation device may be configured to provide an indication when the beaconing signal is received. In one arrangement the beaconing signal can be initiated by a user selecting an icon associated with the aerosol generating device on the display screen of the user device. For example, the user may be able to select an icon associated with the aerosol generating device, as displayed on a map. On receipt of the beaconing signal the aerosol generating device is adapted to provide the indication. For example, the aerosol generating device can vibrate so that it can be easily located by a user.

According to another aspect of the invention there is provided a method comprising the steps of: determining a position of the electronic user device; providing a communicative interaction between the electronic user device and an aerosol generation device via a communication interface in the electronic user device; and storing the position determined by the positioning module in a data storage module, wherein the stored position is associated with the communicative interaction with the aerosol generation device. The method may implement any feature of the preceding aspects.

According to yet another aspect of the invention there is provided a non-transitory computer readable medium comprising instructions which, when executed by at least one processor, cause the at least one processor to perform steps comprising: determining a position of the electronic user device; providing a communicative interaction between the electronic user device and an aerosol generation device via a communication interface in the electronic user device; and storing the position determined by the positioning module in a data storage module, wherein the stored position is associated with the communicative interaction with the aerosol generation device.

According to another aspect of the invention there is provided a method of displaying a position associated with an aerosol generation device on a user interface of an electronic user device, the method comprising: retrieving a position determined by a positioning module from a data storage module, wherein the stored position is associated with a communicative interaction with the aerosol generation device; and generating instructions to display said position on a user interface.

Preferably the method involves receiving instructions from a user interface to locate an aerosol generation device. Preferably the method involves establishing a connection between the electronic user device and the aerosol generation device and providing an indication on the aerosol generation device. Preferably the method involves receiving instructions from a user interface to provide the indication on the aerosol generation device.

According to another aspect of the invention there is provided a method of locating an aerosol generation device, the method comprising: establishing a connection between an electronic user device and the aerosol generation device; receiving instructions from a user interface to locate the aerosol generation device; and providing an indication on the aerosol generation device and/or electronic user device to aid a user in locating said aerosol generation device. Preferably the indication has a property based on a distance between the electronic user device and aerosol generation device.

According to another aspect of the invention there is provided a system for locating an aerosol generation device, the system comprising: an electronic user device; and an aerosol generation device; wherein the electronic user device and aerosol generation device have respective communication interfaces so that they can establish a communicative interaction, and wherein, upon establishment of a communicative interaction, an indication is provided on the aerosol generation device and/or electronic user device to aid a user in locating the aerosol generation device.

According to yet another aspect of the invention a system is provided comprising an electronic user device having a connection interface; and an aerosol generation device; wherein the electronic user device is configured to provide a beaconing signal using the connection interface, and the aerosol generation device is configured to provide an audible alert when the beaconing signal is received.

Features of any one aspect of the invention can be provided with any other aspect of the invention.

Embodiments of the invention are now described, by way of example, with reference to the drawings, in which.

Before describing several embodiments of the system, it is to be understood that the system is not limited to the details of construction or process steps set forth in the following description. It will be apparent to those skilled in the art having the benefit of the present disclosure that the system is capable of other embodiments and of being practiced or being carried out in various ways. As used herein, the term "aerosol generation device" or "electronic cigarette" may include smoking apparatus to deliver an aerosol to a user, including an aerosol for smoking. An aerosol for smoking may refer to an aerosol with particle sizes of 0.5-7 microns. The particle size may be less than 10 or 7 microns. The apparatus may be portable. Portable may refer to the apparatus being for use when held by a user.

As used herein, the term "processor" or "processing resource" may refer to one or more units for processing including as an ASIC, microcontroller, FPGA, microprocessor, digital signal processor (DSP) capability, state machine or other suitable component. A processor may include a computer program, as machine readable instructions stored on a memory and/or programmable logic.

Figure 1:
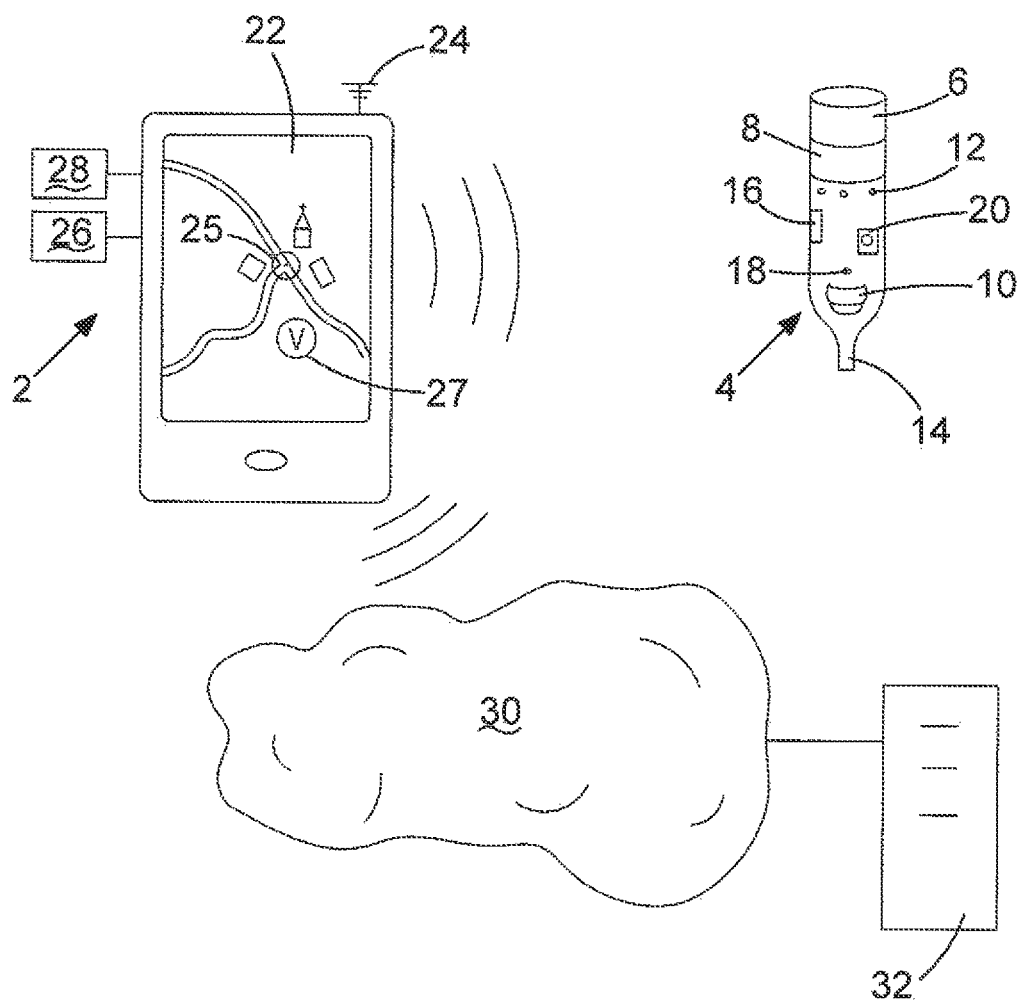
FIG. 1 is a schematic view of a smartphone in communication with an electronic cigarette, in an embodiment of the present invention.

FIG. 1 is a schematic view of a smartphone 2 and an electronic cigarette 4. The electronic cigarette 4, which is an aerosol generation device, comprises a battery 6 and a reservoir 8 for storing vaporisable liquid. The vaporisable liquid in the reservoir 8 can be supplied to an atomiser 10, powered by the battery 6. Air inlets 12 are provided in the body of the electronic cigarette, and an airflow can be generated by a user inhaling via a mouthpiece 14. The airflow can draw air into the air inlets 12 and past the atomiser 10 so that the user can inhale air which includes vaporised liquid from the reservoir 8.

Alternative aerosol generation devices may be provided that are not based on vaporisable liquid. In one example, an aerosol generation device can be supplied with capsules containing conventional tobacco. These capsules can be heated, without burning the tobacco, to release vapours that can be carried away from the capsule in an airflow.

The electronic cigarette 4 comprises a Bluetooth® transmitter 16, which can be used to establish a communicative interaction with a corresponding Bluetooth transmitter 24 in the smartphone 2. The electronic cigarette 4 also comprises an indicator light 18 and a motor 20 which can be used to generate a vibration. The indicator light 18 and the motor 20 are electrically coupled to the battery 6.

The smartphone 2 comprises an antenna 24 which can be used for wireless communication with the electronic cigarette 4. The smartphone also comprises electronics for wireless communication based on cellular technology and Wi-Fi.

The smartphone 2 comprises a GPS receiver 26 that can monitor geographic position. GPS signals are typically only available in outdoor environment, and the smartphone is adapted to determine a position using alternative techniques when GPS signals are not available. A few examples of alternative techniques include Wi-Fi positioning, dead reckoning and cellular positioning. A data storage unit 28 is also provided in the smartphone 2.

The smartphone 2 is communicatively connected to a network 30, such as a cellular network or the internet. A server 32 is connected to the network 30 and arranged for communication with the smartphone 2. In some embodiments the smartphone 2 may communicate with the server 32 in order to store data. This may occur when there is no storage available on the smartphone 2. Thus, the function of the data storage unit 28 may be performed by the server 32 in some embodiments.

Figure 2:
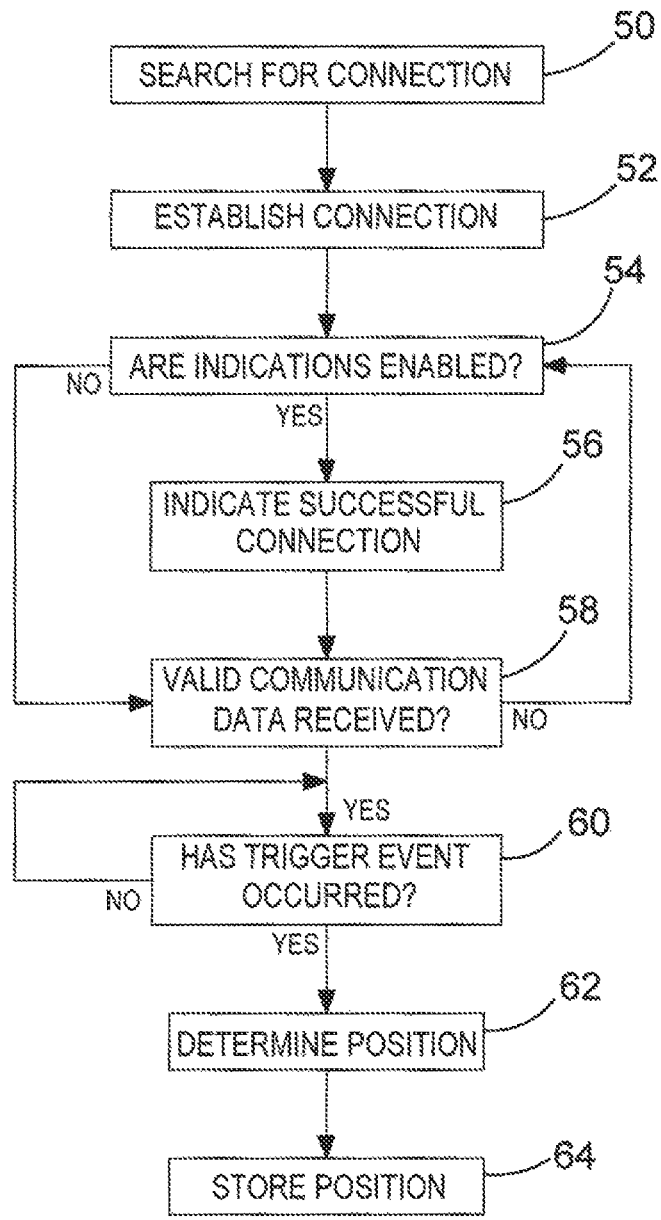
FIG. 2 is a flow diagram showing a sequence of steps that can be undertaken in an embodiment of the present invention.

FIG. 2 is a flow diagram showing steps that can be undertaken in an embodiment of the invention. At step 50 the smartphone 2 and the electronic cigarette 4 search for a connection with one another. At step 52 a connection is established when the two devices are in the same location using, in this example, Bluetooth® protocol.

Indications can be inhibited for the smartphone 2 or the electronic cigarette 4 by selection of an appropriate button by the user. Indications can also be inhibited during a specified use of the devices. For example, indications can be inhibited while the electronic cigarette 4 is being used for vaping as may be detected by depression of a vaping button, or activation of an air pressure sensor. Therefore, at step 54 the smartphone 2 establishes whether indications are enabled for the smartphone 2 and the electronic cigarette 4.

At step 56, an indication is provided on the smartphone 2 and/or the electronic cigarette 4 to indicate that a successful Bluetooth® connection has been established. In one example, this is accomplished by turning on the indicator light 18 on the electronic cigarette 4, and by providing a vibration in the smartphone 2.

At step 58 the smartphone 2 determines whether data are received in the communicative interaction that would prompt the smartphone 2 to store a geographic position. In one example the smartphone 2 is adapted to store a geographic position, as determined by the GPS receiver 26, whenever a successful connection has been established. In this way, the smartphone 2 can maintain a log corresponding to position at different times that a connection is established. In another example, the smartphone 2 is adapted to store a position only on receipt of a particular type of data, or a particular pattern of data from the electronic cigarette 4. For example, the electronic cigarette 4 may be adapted to communicate to the smartphone 2 that a vaping button has been depressed. The electronic cigarette 4 may also be adapted to communicate data regarding a vaping episode including data indicative of the start or end of a user's inhalation. The smartphone 2 is adapted to store a geographic position only upon detection of depression of the vaping button, or upon detection of a vaping episode. In some embodiments these may correspond to trigger events.

At step 60 the smartphone 2 is adapted to determine whether a trigger event has occurred. In addition to the examples above, a trigger event may correspond to the establishment of a communicative interaction with the electronic cigarette 4. In another embodiment the trigger event may correspond to the termination of a communicative interaction with the electronic cigarette 4.

At step 62 the smartphone 2 is adapted to determine a geographic position using the GPS receiver 26. At step 64 the geographic position is stored in data storage 28 in the smartphone 2 or in the server 32, as appropriate. The geographic position is stored along with information that can identify the electronic cigarette 4, such as its serial number, batch number or MAC address. Geographic positions may be stored in the data storage unit 28 for several different electronic cigarettes 4.

In use, a user can 'connect' their electronic cigarette 4 to their smartphone 2 in order to exchange data. In this way, the user can monitor the performance of the electronic cigarette 4 using their smartphone and can connect these data to any of a wide variety of internet applications. The smartphone 2 is adapted to store a geographic position in the data storage unit 28 on each occasion that a communicative interaction is established. Thus, the smartphone 2 can maintain a log corresponding to position at different times.

Figure 3:
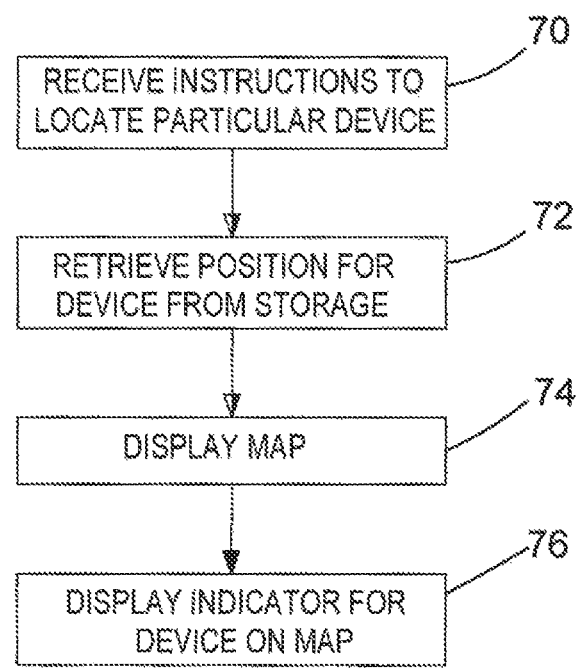
FIG. 3 is another flow diagram showing a sequence of steps that can be undertaken in an embodiment of the present invention.

FIG. 3 is a flow chart showing a sequence of steps that can be undertaken when it is desired to display a stored position on a map. At step 70 the smartphone 2 receives instructions to locate a particular electronic cigarette 4. This may be achieved by the user selecting an icon on the display screen 22 that indicates the device type or ID for the desired electronic cigarette. Often a user will have more than one electronic cigarette so this can allow the user to select the desired device. At step 72 the smartphone 2 is adapted to retrieve a stored position for the selected electronic cigarette from the data storage unit 28. In particular, the smartphone 2 can retrieve the most recent stored position for the selected electronic cigarette 4, even if no connection is present between the smartphone 2 and the electronic cigarette 4. At step 74 the smartphone 2 can display the most recent stored position on a map on the display screen 22. At step 76 the smartphone 2 can display an indicator at a position on the map corresponding to the position retrieved from the data storage unit 26. In the example of FIG. 1 the display screen 22 shows a map including the current position of the smartphone 25 and an icon 27 that is indicative of the last known geographic position 27 of the electronic cigarette 4. In this way, the user can be assisted in locating the electronic cigarette 4, if it has been misplaced.

The icon 27 is displayed on the map in a first colour when no connection is present between the smartphone 2 and the electronic cigarette 4. The icon 27 is displayed in a second colour when a connection is established.

Figure 4:
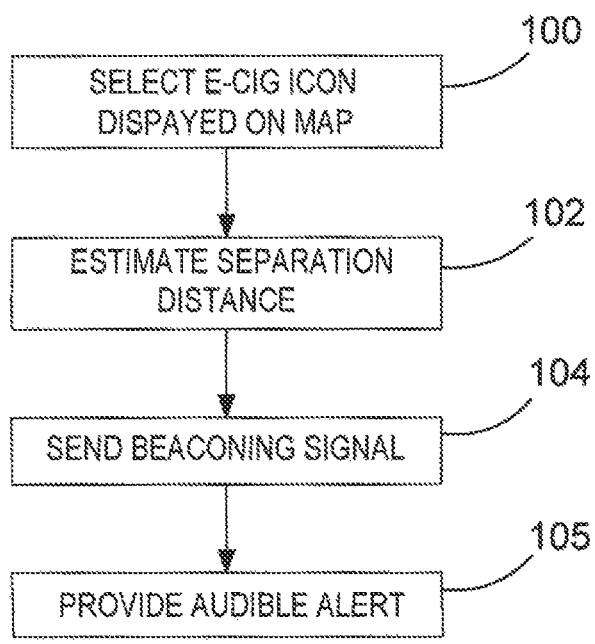
FIG. 4 is another flow diagram showing a sequence of steps that can be undertaken in an embodiment of the present invention.

The smartphone 2 can also be used to provide a beaconing signal to the electronic cigarette 4 when a connection is established between the two devices. FIG. 4 is a flow chart showing a sequence of steps that can be undertaken in a beaconing operation. At step 100 the user can indicate that they wish to send a beaconing signal to the electronic cigarette 4. In this example, this is achieved by the user selecting the icon 27 for the electronic cigarette 4 displayed on the map. At step 102 the smartphone 2 is configured to determine an estimated physical separation to the electronic cigarette 4. This can be achieved in different ways, depending on the method used to establish a communicative interaction. If a cable is used then the estimated separation may correspond to the normal length of the cable. If Bluetooth® is used then the estimated separation may be inversely proportional to the signal strength received at the smartphone 2. At step 104 the smartphone 2 is configured to transmit a beaconing signal to the electronic cigarette 4. The beaconing signal is received at the electronic cigarette 4 and, in response, at step 105 the electronic cigarette 4 can issue an audible alert. In this example the motor 20 in the electronic cigarette 4 is used to generate a vibration. Properties of the vibration generated by the motor 20 are proportional to the estimation of the separation distance calculated at step 102. In one arrangement the period between a series of vibrations can be selected according to the estimated separation distance. The vibrations are preferably loud enough to be heard by the user so that they can easily locate the electronic cigarette 4. The vibration can be cancelled by the smartphone 2 or the electronic cigarette 4 by pressing a button or a selectable item on the display screen 22.

Figure 5:
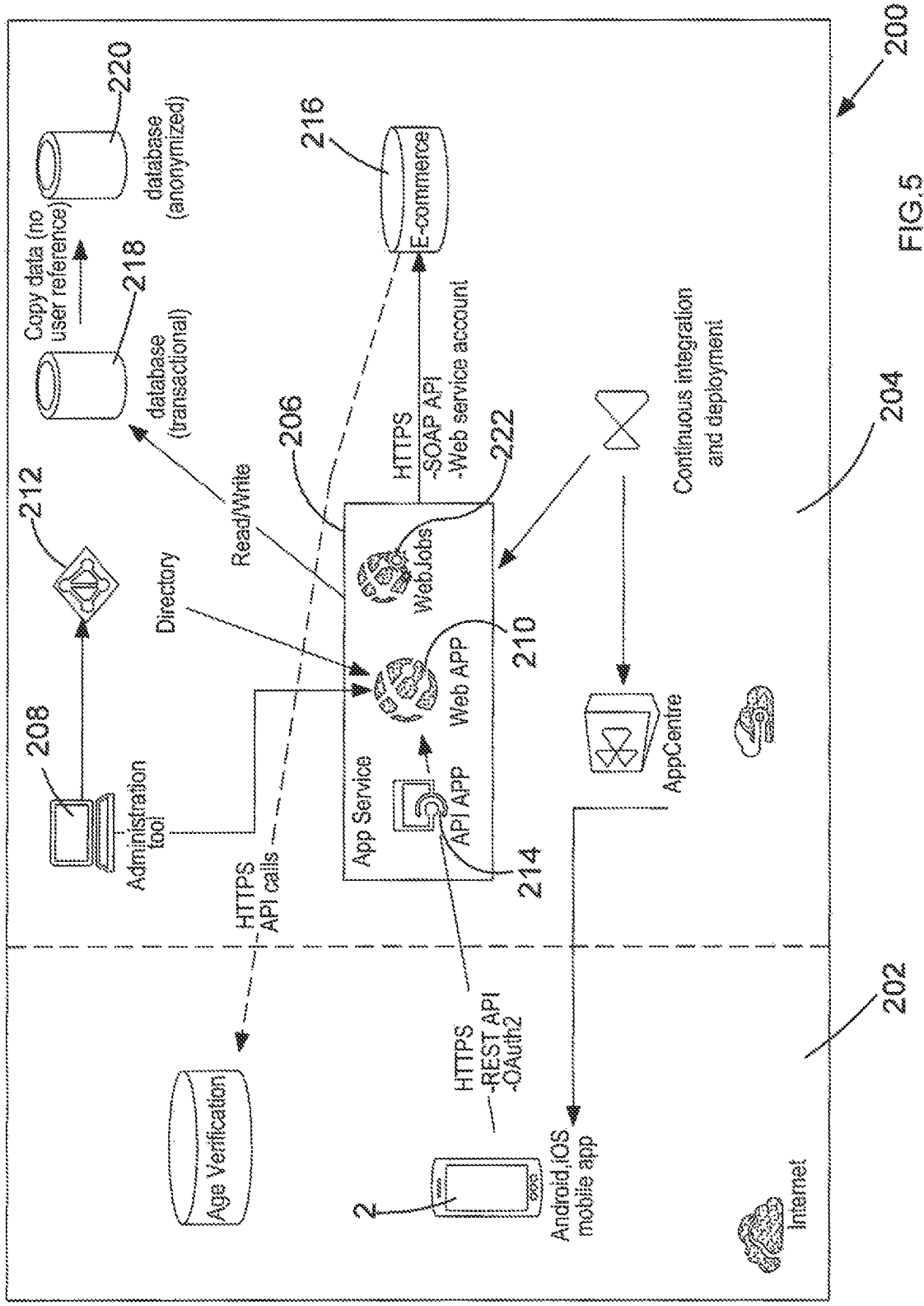
FIG. 5 is a schematic view of a system in an embodiment of the present invention.

FIG. 5 is an exemplary embodiment of a system according to the present invention including a smartphone 2 within a system 200 based on two parts: a frontend system 202 and a backend system 204. The frontend system 202 includes the smartphone 2, where a mobile application is provided in the smartphone 2. The mobile application allows a user to provide registration, age verification and login details, input data or make user requests, such as online purchases or store locator queries, to the backend system 204. The mobile application is adapted to store in the smartphone data storage 28, or send to the network 30, geographic positions of one or more electronic cigarettes 4, where a user can use the mobile application to locate a particular electronic cigarette. The geographic position is based on the latitude and longitude of an electronic cigarette after a trigger event has occurred and the time and location details are provided to the data storage or network. A user may also provide information to the backend system 204 via an internet application, or web app.

The backend system 204 receives user information, user requests and specific electronic cigarette information from the frontend system 202 at an App service 206. The backend system 204 includes:

Administration tool 208 and Administration Web App 210: these components are the administrative part of the backend system 204. Roles, permissions, user management system configuration and administrative activities on certain system functions are handled, and the Admin Web App 210 makes calls to an active directory 212 for a single sign on user authentication mechanism.

Active directory 212: this component performs user or client verification in actions including: registration, login, buy online and store locator. The active directory 212 is used to tenant the administration web app 210 and an API (application program interfaces) app 214, based on a cloud directory and identity management service. Active directory 212 combines core directory services, advanced identity governance and application access management.

API App 214: The API App contains all the APIs exposed by the backend system 204 and the calls to E-commerce API 216. The E-commerce API 216 receives data for electronic commerce actions, such as registration, login, buy online and store locator. Users or clients accessing the backend system 204 through API App 214. To authorise access in the API App 214, the mobile application requires an access token from active directory 212.

Transactional database 218: the transactional database may be, for instance, a structured query language, SQL, database or similar type of database in which Administration Web App 210 and API App 214 reads and writes data to. The transactional database contains information from the whole backend system. A project or an SQL project is created for each part of the database containing all necessary scripts: for creating tables, functions and stored procedures. The transactional database is split in three schemas: the administration schema, the application schema, and the security schema.

Anonymized database 220: this component, which may be based on SQL, contains only statistical information, without any information about a user. Data is copied without any information about the user from Transactional database 218, the process being done by WebJobs component 222. Data anonymization is a type of information sanitization whose scope is to protect privacy. Anonymized database 220 contains a certain set of anonymized data related to vaping activities and will be available for reporting purposes. Personal identifiable information from data set will be removed so that the people whom the data describe remain anonymous. There are no references to users in the anonymized data set.

WebJobs component 222: this component contains two web jobs, containing C# codes. One WebJob is used to copy data from transactional database 218 to anonymized database 220. The other WebJob is implemented for data purge from transactional database 218 every six months or other predetermined period of time.

The backend system 204 is structured into different layers where each layer has its own role to help the communication between the frontend system 202 and the backend system 204. This approach exposes some of the core functionality as services for user or client applications (e.g. using Android and iOS) to consume, which helps to minimise the impact of adding new APIs or new business logic to the overall system. The layers separate database logic, business logic, application program interfaces (API) and administration tools in provided services to a user mobile application.

Figure 6:
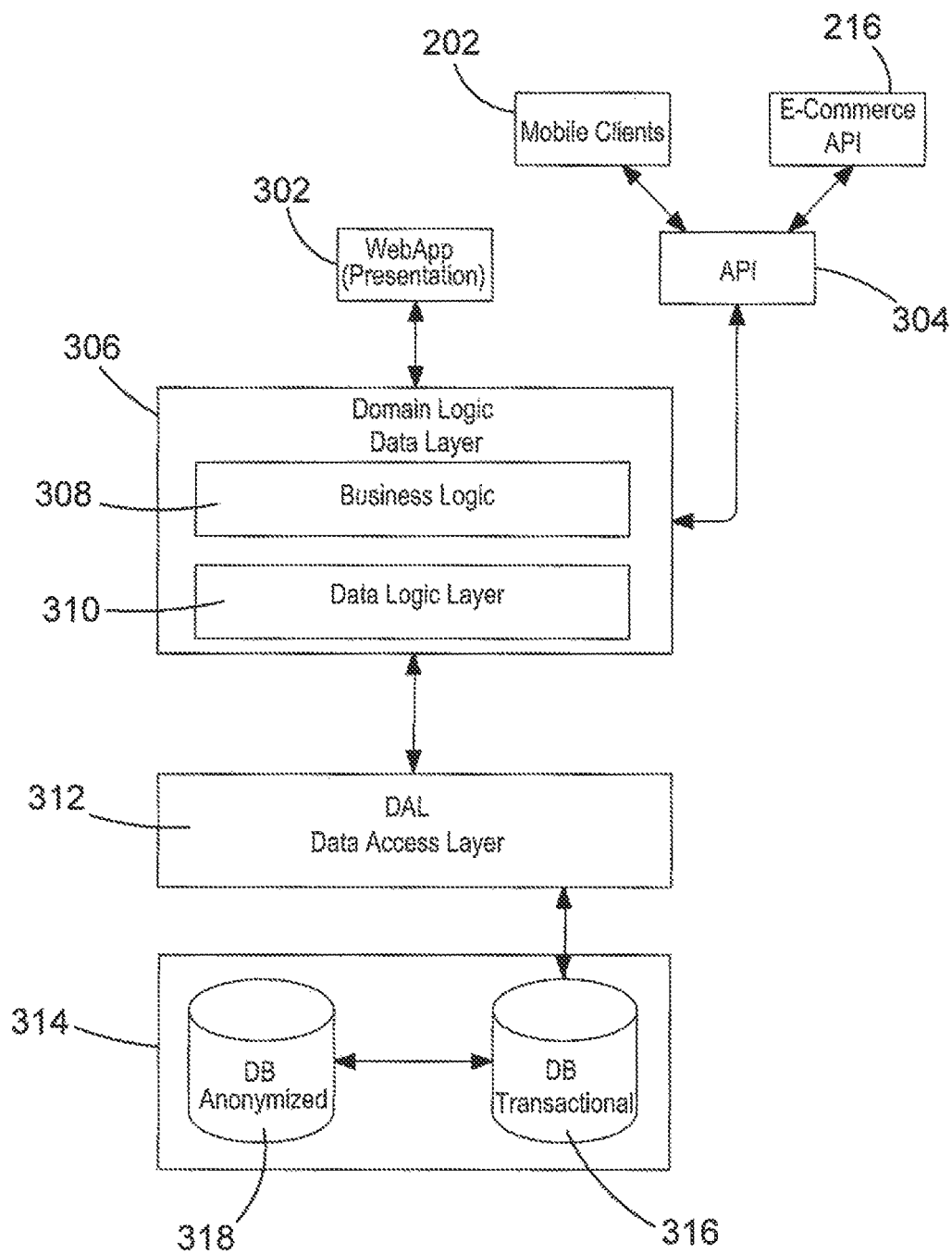
FIG. 6 is another schematic view of a system in an embodiment of the present invention.

FIG. 6 shows a representation of a layered application that may be implemented in the backend system 204 (shown in FIG. 5) according to an embodiment of the present invention. Each layer helps the communication of the user or client with the databases and the APIs.

The layers are described in more detail below:

WebApp layer 302: The WebApp layer 302 (or presentation layer) is a web application developed which implements a presentation layer for administration. This application maintains a session, being scalable, also maintains the E-commerce API and mobile clients, iOS and Android, and the calls between backend application and clients.

API layer 304: This layer is a separate project built to manage the APIs, a stateless application to realize the calls between E-commerce API and mobile clients, iOS and Android, and the calls between backend application and clients. This layer will send and receive data from the domain logic layer. The API layer 304 contains the routes to the backend, the methods to communicate with the domain logic layer 306, using the domain logic models, and API versioning.

Domain logic layer 306: The domain logic layer 306 is built to separate the business logic from the rest of the backend application. This layer uses a generic repository, domain logic models and dependency injection. The domain logic layer includes a business layer 308 and a data model layer 310.

Data access layer 312: The data access layer 312 has the role to get the data from a database, creating the models for the tables from database. This layer helps the backend application to communicate with the database, using an Entity framework, data access layer models (code first/database first) and the database context.

Database layer 314: The database layer 314 is split in two different layers: the transactional database layer 316 and the anonymized database layer 318. Both are Projects that can be based on SQL and are developed for creating the tables, the functions and the stored procedures needed to receive data from a database. The anonymized database layer 318 is created to store different statistics, for example: the number of puffs, how often the cigarette is used, but without storing personal data about the user in this table. The transactional database layer 316, has the role to create the tables, the functions and the stored procedures to store data about the administration, such as: actions, firmware version, localization version, and about the applications, such as: about the capsule, the device, the user and also about vaping activity of the user.

Figure 7:
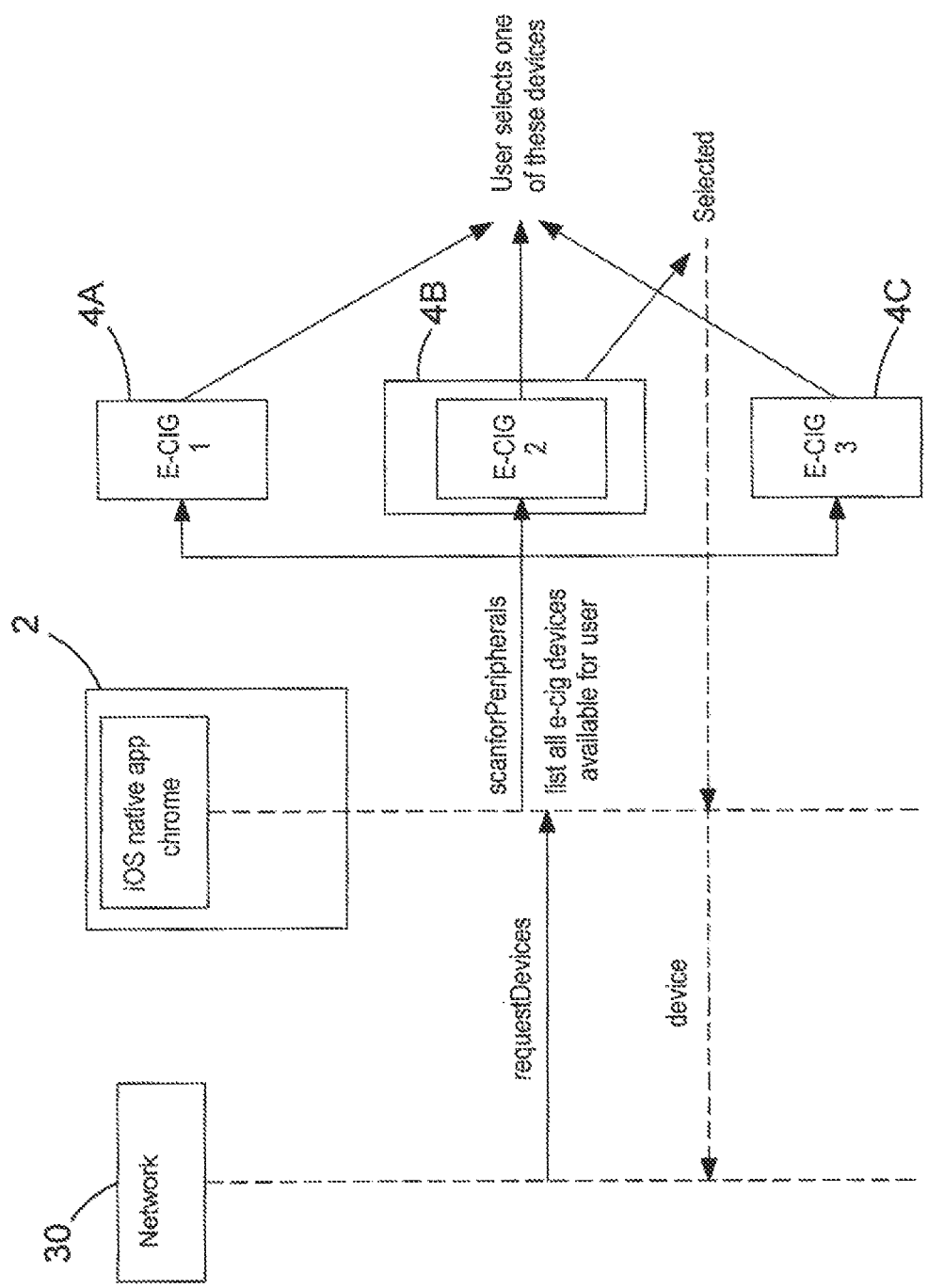
FIG. 7 is another schematic view of a smartphone in communication with a network and an electronic cigarette, in an embodiment of the present invention.

FIG. 7 shows a schematic representation of the communication between the network 30 via server 32, smartphone 2, and a plurality of electronic cigarette devices according to an embodiment of the invention. The smartphone 2 and any connected electronic cigarette devices may be located in the frontend system 202 (shown in FIG. 5), and the network 30 allows for communication between the front end system 202 and the backend system 204 (shown in FIG. 5). The network 30 can perform a scan of electronic cigarette devices for communication with the network. A command is sent to a mobile application on the smartphone 2 which then scans for all the available cigarette devices 4A, 4B, 4C available to a user. Electronic cigarette devices 4A, 4B, 4C are connected to the smartphone 2 via Bluetooth®. The mobile application displays a list of the available devices for the user to select a device from the list, and the application sends information relating to the selected device to the network 30.

After a connection is established the network 30 can communicate with an electronic cigarette device 4B through the mobile application in a smartphone 2. The mobile application can read or write data from/to the cigarette device 4B, and the network can notify the mobile application when a change has occurred, e.g. when a capsule requires changing/replacing or battery power in the device is low.

Additional functions, or services, are as follows:

Authentication: This step is required to get a device's information: device id, device mac address, capsule information and to communicate with the device. The process is done using characteristics for reading, writing and notifying.

Capsule info: This service is used to read capsule information: puffs left, nicotine left, etc. The PWA app can read capsule info and can be notified by an electronic cigarette device when the capsule is changed.

Device info: This service is used to read information about the device using a read characteristic.

Device settings: This service is used to change device settings (sleep time, max puff duration) and also to use functionalities like: find device, reboot device, reset device using the write characteristics.

Event info: This service is used to receive notifications from device to the network when a malfunction has occurred (software over temperature, dry vape, hardware over temperature)

Over the air: This service is used to update, from the network, the firmware of the electronic cigarette device based on write and notify characteristics.

Vaping: This service is used to get information when user is vaping. So, the network is notified when user is smoking, getting the duration, the temperature, info about the liquid, using the notify and write functions/characteristics.

If an internet connection is lost, communication between the mobile application and the device 4B can work in the same way, and information about the device 4B is saved in a data storage of the smartphone 2. Local storage is a read-only property that allows the mobile application to access the data storage 28 in the smartphone 2 from mobile application. Web storage is per origin (per domain and protocol). Unlike cookies and session storage, local storage does not have an expiration date (data can be stored until removed). As an example, if the puffs or events could not be sent because of no internet connection, the information or data are saved in the smartphone data storage which then are sent to the network or backend system when internet connection is established. The same approach is done for device information (id, mac address, serial code, name, Bluetooth® version, temperature, capsule information), saving temporary values that should be sent to the backend system later.

The invention claimed is:

1. A method of locating an aerosol generation device, comprising:
    outputting, by one or more processors, for display on a display of a user device, an icon indicating a last stored position of an aerosol generation device on a map;
    outputting, by the one or more processors, for display on the display of the user device, a graphic element, wherein the graphic element is selectable after communicative interaction is established between the aerosol generation device and the user device;
    receiving, by the one or more processors, an input indicating a selection of the graphic element; and
    transmitting, by the one or more processors, and in response to the received input, a signal to trigger an indication by the aerosol generation device.

2. The method of claim 1, wherein the last stored position of the aerosol generation device is a position of the user device stored when the user device is in communicative interaction with the aerosol generation device.

3. The method of claim 2, wherein the last stored position of the aerosol generation device is the last position of the user device stored when the user device loses communicative interaction with the aerosol generation device.

4. The method of claim 3, wherein the last stored position of the aerosol generation device is retrieved from memory within the user device or memory within a server remotely located from the user device.

5. The method of claim 1, further comprising:
    outputting, by the aerosol generation device in response to receiving the signal, one or more audible indications.

6. The method of claim 1, further comprising:
    outputting, by the aerosol generation device in response to receiving the signal, one or more visual indications.

7. The method of claim 1, further comprising:
    outputting, by the aerosol generation device in response to receiving the signal, one or more audible indications and one or more visual indications.

8. The method of claim 1, wherein the communicative interaction between the aerosol generation device and the user device is via a Bluetooth connection.

9. The method of claim 8, wherein the signal is transmitted over the Bluetooth connection.

10. The method of claim 1, further comprising, before the communicative interaction is established:
    searching, by the aerosol generation device, for a connection with the user device; and
    establishing the communicative interaction after the aerosol generation device finds a connection with the user device.

11. The method of claim 1, further comprising, before the communicative interaction is established:
    searching, by the user device, for a connection with the aerosol generation device; and
    establishing the communicative interaction after the user device finds a connection with the aerosol generation device.

12. A system comprising:
    one or more processors configured to:
        output, for display on a display of a user device, an icon indicating a last stored position of an aerosol generation device on a map;
        output, for display on the display of the user device, a graphic element, wherein the graphic element is selectable after communicative interaction is established between the aerosol generation device and the user device;
        receive an input indicating a selection of the graphic element; and
        transmit, in response to the received input, a signal to trigger an indication by the aerosol generation device.

13. The system of claim 12, wherein the last stored position of the aerosol generation device is a position of the user device stored when the user device is in communicative interaction with the aerosol generation device.

14. The system of claim 13, wherein the last stored position of the aerosol generation device is the last position of the user device stored when the user device loses communicative interaction with the aerosol generation device.

15. The system of claim 14, wherein the one or more processors are further configured to receive the last stored position of the aerosol generation device from memory within the user device or memory within a server remotely located from the user device.

16. The system of claim 12, further comprising the aerosol generation device.

17. The system of claim 16, wherein the aerosol generation device is configured to output, in response to receiving the signal, one or more audible indications and/or one or more visual indications.

18. The system of claim 12, further comprising:
a communication interface, wherein the communicative interaction between the aerosol generation device and the user device is established via the communication interface.

19. The system of claim 18, wherein the communication interface establishes the communicative interaction using a Bluetooth or Wi-Fi protocol.

20. The system of claim 18, wherein, before the communicative interaction is established the one or more processors are further configured to search for a connection with the aerosol generation device via the communication interface.

21. The system of claim 18, further comprising the aerosol generation device, wherein, before the communicative interaction is established, the aerosol generation device is configured to search for a connection with the user device.

* * * * *